United States Patent [19]

Baker et al.

[11] Patent Number: 5,420,269
[45] Date of Patent: May 30, 1995

[54] 3-FLUOROSULFONYLOXYCEPH-3-EM COMPOUNDS

[75] Inventors: Stephen R. Baker, Cicero; Chester Sapino, Jr., East Syracuse, both of N.Y.; Gregory P. Roth, Cheshire, Conn.

[73] Assignee: Bristol-Myers Squibb Co, New York, N.Y.

[21] Appl. No.: 77,825

[22] Filed: Jun. 15, 1993

Related U.S. Application Data

[60] Division of Ser. No. 603,872, Oct. 31, 1990, Pat. No. 5,245,027, which is a continuation-in-part of Ser. No. 439,767, Nov. 19, 1989, abandoned.

[51] Int. Cl.$^6$ ................. C07D 487/04; A61K 31/435
[52] U.S. Cl. .................................................. 540/205
[58] Field of Search ......................... 540/205; 514/210

[56] References Cited

U.S. PATENT DOCUMENTS

| | | |
|---|---|---|
| 4,520,022 | 5/1985 | Hoshi et al. |
| 4,820,816 | 4/1989 | Evans et al. ................ 540/205 |
| 4,820,832 | 4/1989 | Cook et al. |
| 4,847,373 | 7/1989 | Baker et al. |
| 4,870,168 | 9/1989 | Baker et al. |

OTHER PUBLICATIONS

W. J. Scott, "*J. Amer. Chem. Soc.*", 106 4630–4632 (1984), Palladium–Catalyzed Coupling of Vinyl Triflates with Organostannanes. A Short Synthesis of Pleraplysillin–1.

W. J. Scott, et al., "*J. Amer. Chem. Soc.*", 108, 3033–3040, (1986), Palladium–Catalyzed Coupling of Vinyl Triflates with Organostannanes. Synthetic and Mechanistic Studies.

J. K. Stille, et al., "*J. Amer. Chem. Soc.*", 109, 813–817 (1987), Stereospecific Cross–Coupling of Vinyl Halides with Vinyl Tin Reagents Catalyzed by Palladium.

American Chemical Society, 196th National Meeting, Los Angeles, CA, Sep. 25–30, 1988, Div. of Organic Chemistry, Abstract No. 32.

American Chemical Society, 196th National Meeting, Los Angeles, CA, Sep. 25–30, 1988, Div of Organic Chemistry, Abstract No. 402.

*Primary Examiner*—Nicholas Rizzo
*Attorney, Agent, or Firm*—Aldo A. Algieri

[57] ABSTRACT

3-Fluorosulfonyloxyceph-3-ems having a protected amino or acylamino group in the 7-position are subject to carbon-carbon bond formation at the 3-position by means of a palladium catalyzed coupling reaction with substituted organostannanes. A process for preparing cefprozil is disclosed.

2 Claims, No Drawings

3-FLUOROSULFONYLOXYCEPH-3-EM COMPOUNDS

CROSS-REFERENCE TO RELATED APPLICATION

This application is a division of pending U.S. Ser. No. 07/603,872 filed Oct. 31, 1990, now U.S. Pat. No. 5,245,027, which is a continuation-in-part of U.S. Ser. No. 07/439,767 filed Nov. 11, 1989, now abandoned.

BACKGROUND OF THE INVENTION

1. Field of the Invention

This invention refers to a process for the production of cephem, carba(dethia)cephem, and oxa(dethia)-cephem compounds, and to 3-(fluorosulfonyl)oxy substituted cephem, oxacephem and carbacephem intermediates useful in this process.

2. Description of Related Art

Hoshi et al., U.S. Pat. No. 4,520,022 (May 28, 1985), discloses cephalosporin antibiotics having the 1-propenyl group in the 3-position which are represented by the following formula in which $R^1$ and $R^2$ are H, OH, $OCH_3$, or Cl.

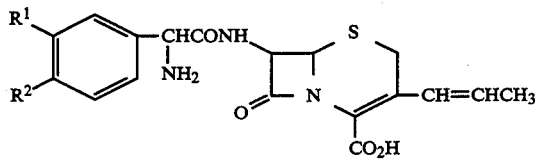

The 1-propenyl group of the Hoshi et al. compounds is preferably in the (Z) configuration because of enhanced antibacterial activity compared to the (E) configuration. These compounds are produced by reacting a 3-halomethyl cephalosporin with a triarylphosphine to yield a phosphoranyl intermediate which is then treated with an aldehyde to form the propenyl or substituted propenyl group.

The foregoing process affords a mixture of the cis(Z)- and trans(E)-isomers which requires costly separation or adjustment of process conditions to obtain the preferred, more antibacterially active cis(Z)-isomer. The overall yield of desired cis(Z)-isomer based on starting material is thus reduced by the amount of the trans(E)-isomer produced.

More recently palladium catalyzed coupling methods have been applied to the formation of alkenyl substituents at the 3-position of the cephalosporin nucleus in order to avoid formation of the undesired isomer and to improve yields. Allylic coupling of 3-halomethylcephems with vinyl stannanes under the influence of Pd(0) compounds, metal halides, and tris-(2-furyl)phosphine led to the production of novel cephalosporins (S. R. Baker et al. U.S. Pat. No. 4,847,373 patented Jul. 11, 1989). The method of W. J. Scott et al., J. Amer. Chem. Soc., 106, 4630–4632 (1984) for the Pd(0) compound/LiCl catalyzed coupling of a cyclohexenyl triflate with vinyl tributylstannane has been adapted to the reaction of a 3-trifloxyceph-3-em with (Z)-1-propenyl tributyl-stannane to produce various 3-((Z)-1-propenyl)ceph-3-ems (S. R. Baker et al., U.S. Pat. No. 4,870,168 patented Sep. 26, 1989).

Further research on the reaction scope and optimization of reaction conditions for the palladium catalyzed coupling of vinyl triflates and vinyl stannanes has been reported in Scott and Stille, J. Amer. Chem. Soc. 108, 3033–3040 (1986), and Stille and Groh, J. Amer. Chem. Soc. 109, 813–817 (1987).

The coupling of a 3-trifloxyceph-3-em with an organic tributylstannane reagent in the presence of $PdCl_2(CH_3CN)_2$ without the aid of the phosphine reagent or LiCl required in the W. J. Scott et al. method (op. cit.) was reported by G. K. Cook and J. H. McDonald III at the 196th American Chemical Society National Meeting, Los Angles, Calif. Sep. 25–30, 1988, Division of Organic Chemistry, Abstract No. 32.

SUMMARY OF THE INVENTION

The present invention provides novel 3-(fluorosulfonyl)oxy substituted cephems, oxacephems, and carbacephems having formula I:

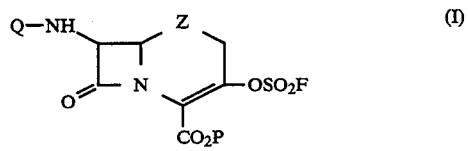

wherein Z is sulfur, oxygen, sulfoxide, sulfone, or methylene; Q is hydrogen, an amine protecting group conventionally used in cephalosporin synthesis, or the acyl group of a known 7-acylaminocephalosporin antibiotic; and P is hydrogen, a carboxy protecting group conventionally used in cephalosporin synthesis, a cation, or a physiologically hydrolyzable ester group.

The present invention also provides a process for preparing cephems, oxacephems, and carbacephems having an alkenyl, alkynyl, aryl, or heterocyclic group at the 3-position of the cephem nucleus. The process comprises reacting a 3-sulfonyloxy substituted cephem, oxacephem, or carbacephem reactant with an organostannane in the presence of a Pd(II) or Pd(0) catalyst; the 3-sulfonyloxy group is selected from fluorosulfonyloxy, 4-nitrobenzenesulfonyloxy, and 4-bromobenzenesulfonyloxy. The present process represents an improvement over the invention described U.S. Pat. No. 4,870,168 in that the costly reagent used therein, 3-trifloxyceph-3-em, has been replaced with the relatively inexpensive reagents of the instant invention.

DETAILED DESCRIPTION OF THE INVENTION

As used in the specification, unless otherwise indicated explicitly or by context, "alkyl", "alkenyl", "alkynyl", "alkadienyl", and like terms include both straight and branched carbon chains. Compounds containing the fragment

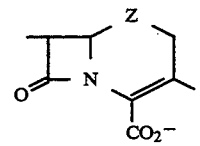

are referred to as "cephem" when Z is sulfur, as "oxacephem" when Z is oxygen, and as "carbacephem" when Z is methylene. The various asymmetric carbon atoms of the azabicyclo ring system have the same stereochemical configuration as that of the cephalosporin antibiotics presently in wide-spread medical use, which configuration is related to the fermentation product cephalosporin C.

One aspect of the present invention provides 3-(fluorosulfonyl)oxy substituted cephems, oxacephems, and carbacephems of formula I

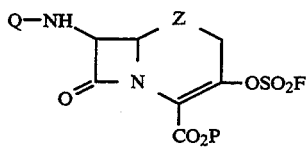

wherein Z is sulfur, oxygen, sulfoxide (—SO—), sulfone (—SO$_2$—), or methylene (—CH$_2$—); Q is hydrogen, an amine protecting group conventionally used in cephalosporin synthesis, or the acyl group of a known 7-acylaminocephalosporin antibiotic; and P is hydrogen, a carboxy protecting group conventionally used in cephalosporin synthesis, a cation, or a physiologically hydrolyzable ester group.

"A carboxy protecting group" may be any that is readily replaced with hydrogen under conditions which do not affect other functional groups in the molecule. Such groups and conditons suitable for their replacement are described in "Protective Groups in Organic Synthesis" by Theodora W. Greene, John Wiley & Sons, New York 1981 Chapter 5, pp 151-192. Examples of carboxy protecting groups in cephalosporin synthesis include, but are not limited to, optionally substituted lower alkyl such as methyl, ethyl, trichloromethyl, trichloroethyl, tertiary butyl, methoxymethyl, methoxyethyl, acetoxymethyl, acetoxyethyl, and methanesulfonylmethyl; optionally substituted aralkyl such as diphenylmethyl, trityl, monomethoxytrityl, benzyl, 4-methoxybenzyl, and 4-nitrobenzyl; silyl groups such as trimethylsilyl and t-butyldimethylsilyl; lower alkenyl such as vinyl and allyl; and aryl such as phenyl, tolyl; etc.

"A cation" includes, but is not limited to, alkali metal, e.g. sodium, lithium, and potassium; alkaline earth metal, e.g. calcium and magnesium; ammonium; and alkylammonium, e.g. trimethylamine and triethylamine.

"A physiologically hydrolyzable ester" includes, but is not limited to, a lower alkoxycarbonyloxyalkyl group, e.g. ethoxycarbonyloxyethyl; a lower alkylcarbonyloxyalkyl group, e.g. acetoxymethyl and pivaloyloxymethyl; and an (2-oxo-1,3-dioxolene-4-yl)methyl group, e.g. (4-methyl-2-oxo-1,3-dioxol-5-yl)methyl.

"An amino protecting group" of the sort conventionally used in cephalosporin synthesis includes, but is not limited to, lower alkanoyl or substituted lower alkanoyl, e.g. formyl, acetyl, chloroacetyl, and trifluoroacetyl; aroyl or substituted aroyl, e.g. benzoyl, 4-methoxybenzoyl, and 4nitrobenzoyl; aralkyl, substituted aralkyl, aralkylidene, or substituted aralkylidene, e.g. benzyl, diphenylmethyl, trityl, nitrobenzyl, methoxybenzyl, and benzylidene; halogenated alkyl, e.g. trichloromethyl, trichloroethyl, and trifluoromethyl; alkoxycarbonyl or substituted alkoxycarbonyl, e.g. methoxycarbonyl, ethoxycarbonyl, t-butoxycarbonyl, cyclohexyloxycarbonyl, and trichloroethoxycarbonyl; aralkoxycarbonyl or substituted aralkoxy-carbonyl, e.g. benzyloxycarbonyl, methoxybenzyloxycarbonyl, and nitrobenzyloxycarbonyl; an unsubstituted or substituted trialkylsilyloxycarbonyl or triarylsilyloxycarbonyl; and trialkylsilyl or triarylsilyl groups, e.g. trimethylsilyl and t-butyldimethylsilyl. Amino protecting groups are also described in the aforementioned Greene textbook beginning on page 218.

"Acyl group of a known 7-acylaminocephalosporin antibiotic" refers to the substituent on the 7-amino group of a known cephalosporin antibiotic and may be represented by the formula R—C(O)—. Examples of R include, but are not limited to,

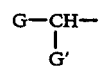

wherein G may be a substituted or unsubstituted aryl, heterocyclic, or cyclohexadienyl group, e.g. phenyl, thienyl, thiazolyl, thiadiazolyl, imidazolyl, pyridyl, tetrazolyl, 1,4-cyclohexadienyl, and furyl; the substituents for the groups may be 1 to 3 of the same or different groups selected from halogen, hydroxy, amino, alkoxy, alkylamino, dialkylamino, alkanoyloxy, carboxy, nitro, cyano, and alkoxycarbonyl; G' may be hydrogen, hydroxy, amino, monoalkylamino, dialkylamino, alkanoylamino, alkanoyloxy, carboxy, and sulfo;

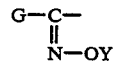

wherein G has the same meaning given above, and Y is hydrogen, $C_{1-6}$alkyl, or $C_{1-6}$alkanoyl;

(c) G—B—CH$_2$— wherein G has the same meaning given above, and B is oxygen or sulfur; and

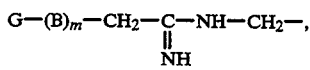

where G, and B have the meanings given above, and m is 0 or 1.

Some specific examples of "acyl group of a known 7-acylaminocephalosporin antibiotic" include 2-amino-2-phenylacetyl, 2-amino-2-(4-hydroxy)phenylacetyl, 2-thienylacetyl, phenylacetyl, 2-hydroxy-2-phenylacetyl, 2-acetoxy-2-phenylacetyl, 1-tetrazolylacetyl, [(2-amino-4-thiazolyl) (methoxyimino)]acetyl, phenoxyacetyl, and [(2-furanyl) (methoxyimino)]acetyl.

It will be appreciated that the above listings serve only to illustrate what the various terms may include; these listings are by no means exhaustive and are not to be construed as limiting.

A preferred embodiment of formula I provides compounds wherein Z is sulfur. Another preferred embodiment provides compounds of formula I where Z is methylene.

Another preferred embodiment of formula I provides compounds wherein Q is an amine protecting group. More preferably, the protecting group is t-butoxycarbonyl or benzyloxycarbonyl.

Another preferred embodiment of formula I provides compounds wherein Q is 2-amino-2-phenylacetyl, 2-amino-2-(4-hydroxy)phenyl-acetyl, 2-thienylacetyl, phenylacetyl, 2-hydroxy-2-phenylacetyl, 2-acetoxy-2-phenylacetyl, 1-tetrazolylacetyl, [(2-amino-4-thiazolyl)-(methoxyimino)]acetyl, phenoxyacetyl, [(2-furanyl)-(methoxyimino)]acetyl. More preferably Q is selected from 2-amino-2-phenylacetyl, 2-amino-2-(4-hydroxy)-phenylacetyl, phenylacetyl, and phenoxyacetyl.

Another preferred embodiment of formula I provides compounds wherein P is a carboxy protecting group selected from t-butyl, benzyl, diphenylmethyl, trityl, 4-nitrobenzyl, and 4-methoxybenzyl. More preferably P is selected from t-butyl, diphenylmethyl and 4-methoxybenzyl.

Compounds of formula I are prepared by acylation of the corresponding 3-hydroxy substituted compound of formula II, preferably wherein the 4-carboxyl group thereof is protected by a readily removable blocking group, with an appropriate sulfonylating agent, e.g. fluorosulfonic acid or more preferably fluorosulfonic anhydride. A typical procedure for the preparation of compounds of formula I is depicted in the following scheme, and discussed further below.

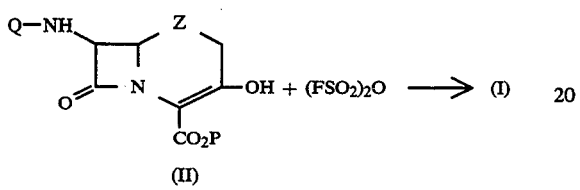

The fluorosulfonic anhydride is allowed to react with the starting material of formula II under conditions which are themselves known for the formation of enol esters with the anhydride reagent. Conditions similar to those used for the formation of the triflate enol esters in U.S. Pat. No. 4,870,168 cited above are suitable. The reaction is carried out by the addition of at least an equimolar amount, preferably a surplus amount, e.g. 10% to 100% on a molar basis relative to the reactant of formula II, of the anhydride to a solution of the reactant of formula II in an inert organic solvent such as methylene chloride. A base such as a sterically hindered tertiary amine (e.g. diisopropylethylamine) is employed in approximately equimolar amount to the anhydride reactant. The preparative process is carried out in the temperature range of 0° C. to −78° C., and preferably under inert atmosphere.

The starting materials of formula II are prepared by methods known in the art. For example, 3-hydroxycephem (i.e. formula II, Z=sulfur) may be prepared by the process described in U.S. Pat. No. 3,085,737; 3-hydroxy-1-oxacephem (i.e. formula II, Z=oxygen) may be prepared as described in European Patent Application 133,670; and 3-hydroxy-1-carbacephem (i.e. formula II, Z=methylene) may be prepared as described in European Patent Application 211,540.

3-(Fluorosulfonyl)oxy substituted cephems, oxacephems, and carbacephems are useful intermediates for the preparation of compounds of formula III.

Another aspect of the present invention provides a process useful for the preparation of cephems, oxacephems, and carbacephems having formula III

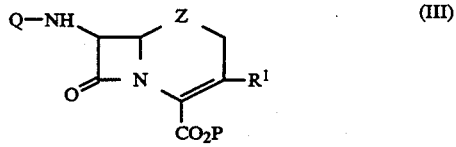

wherein Q, P, and Z have the same meanings given above under formula I. $R^1$ is selected from the group consisting of H, $C_{2-6}$alkenyl, $C_{2-6}$alkynyl, $C_{2-6}$alkadienyl, $C_{6-10}$aryl, substituted $C_{6-10}$aryl, heterocyclic, and substituted heterocyclic wherein said substituted aryl or substituted heterocyclic group bears 1 to 3 groups selected from $C_{1-3}$alkyl, hydroxy, $C_{1-3}$alkoxy, halo, amino, $C_{1-3}$alkylamino, di$C_{1-3}$alkylamino, nitro, carboxyl, $C_{1-3}$alkoxycarbonyl, and cyano. Examples of heterocyclic group include pyridyl, imidazolyl, thiazolyl, furyl, pyrrolyl, thienyl, and isoxazolyl. The present process is particularly useful for preparing compounds of formula III wherein $R^1$ is H, $C_{2-6}$alkenyl, or $C_{2-6}$alkynyl; especially when $R^1$ is $C_{2-6}$alkenyl. Specifically, the present process is useful for the preparation of cefprozil, i.e. 7β-[D-2-amino-2-(4-hydroxyphenyl)acetamido]-3-[(Z)-1-propen-1-yl]ceph-3-em-4-carboxylic acid.

Thus, compounds of formula III are prepared from a compound of formula IV according to the following scheme:

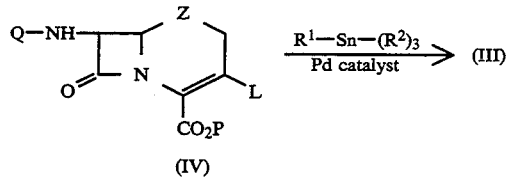

Q, Z, and P are as defined above, and L is selected from the group consisting of fluorosulfonyloxy, 4-nitrobenzenesulfonyloxy, and 4-bromobenzenesulfonyloxy. Compound of formula IV is reacted with an organostannane of the formula $R^1$—Sn—$(R^2)_3$ wherein $R^1$ is as defined above and $R^2$ is an organic group which is known to be suitable for use in organostannane coupling processes, e.g. $R^2$ is $C_{1-6}$alkyl such as butyl, in an inert organic solvent and in the presence of from 1 to 10 mole percent of a Pd(II) or a Pd(0) catalyst.

The 3-(fluorosulfonyl)oxy substituted starting materials of the above scheme are prepared as described hereinabove. The 3-[(4-nitrobenzenesulfonyl)oxy]cephem and the 3-[(4-bromobenzene)sulfonyl)oxy]cephem starting materials are prepared by a modification of the procedures described in U.S. Pat. No. 3,985,737 patented Oct. 12, 1976; the corresponding oxacephem and carbacephem derivatives may be analogously prepared.

In carrying out the present process for the preparation of compounds of formula III, an aprotic organic solvent is selected in which the palladium catalyst compound and the 3-sulfonyloxy compound of formula IV are each soluble. From 1 to 10 mole percent of the palladium catalyst compound relative to substrate of formula IV is used. For substrates of less reactive nature, a greater amount of catalyst within this range is used. The $R^1$ substituted organostannane reactant, palladium catalyst compound, and the 3-sulfonyloxy substituted reactant of formula IV are simply contacted, dissolved, or suspended in the aprotic organic solvent. Reaction takes place spontaneously at room temperature and subsides or comes to completion within a few minutes, usually from 10 minutes to 1 hour. Longer reaction periods of up to 2 or 3 days may be employed in particularly sluggish experimental situations. For commercial scale application periods of from 1 to 4 hours are usually preferred. The particular time period for any given synthesis, and selected scale of operation can be ascertained by assay of the reaction mixture for disappearance of the starting material of formula IV, or for maximal production of product. Thin layer chromatography, high performance liquid chromatography, nuclear magnetic resonance, or spectrophotometric assay methods are applicable.

The palladium catalyzed coupling of a 3-sulfonyloxy substituted cephem, oxacephem, or carbacephem with an organic stannane according to the present process is preferably carried out without the agency of added phosphine ligand or a metal halide. Although a phosphine ligand, such as triphenyl phosphine, and a metal halide, such as zinc chloride, may be included in the reaction milieu, their presence does not confer any advantage to the outcome of the coupling reaction.

In the present process, the starting material of formula IV preferably bears the 3-(fluorosulfonyl)oxy substituent. The $R^2$ group of the organostanne may be ethyl, n-propyl, n-butyl, n-pentyl, n-hexyl, and the like.

The palladium catalyst compound may be of either the Pd(II) or Pd(0) type. Examples of suitable Pd(II) catalyst compounds include palladium acetate, palladium chloride, palladium bromide, palladium iodide, bis-(acetonitrile) palladium dichloride, bis-(phenylacetonitrile)palladium dichloride, palladium nitrate, palladium acetoacetate, palladium sulfate, and palladium oxide. Examples of suitable Pd(0) catalyst compounds include bis(dibenzylideneacetone)palladium, tris(dibenzylideneacetone)dipalladium, and tetrakis(triphenylphosphine)palladium. Preferred palladium catalysts are palladium(II) acetate and tris(dibenzylideneacetone) dipalladium(0).

The aprotic solvent used in the process may be selected from 1-methyl-2-pyrrolidinone, tetrahydrofuran, acetonitrile, dimethylsulfoxide, dimethylformamide, ethers such as glyme, diglyme, and dioxane, hexamethylphosphoramide, acetone, nitromethane, and nitrobenzene, and halogenated hydrocarbons such as methylene chloride. The preferred solvents are 1-methyl-2-pyrrolidone, tetrahydrofuran, acetonitrile, dimethylsulfoxide, methylene chloride, and dimethylformamide. Most preferably, methylene chloride or 1-methyl-2-pyrrolidinone is employed. Mixtures of solvents may also be used.

In a preferred embodiment of the present process, the 3-sulfonyloxycephem is 3-[(fluorosulfonyl)oxy]cephem, the organic stannane is $R^1$-tributylstannane with $R^1$ being $C_{2-6}$alkenyl, the palladium catalyst is palladium-(II) acetate or tris(dibenzylideneacetone) dipallalium (0), and the coupling reaction is performed in 1-methyl-2-pyrrolidinone or methylene chloride without added phosphine and metal halide ligands.

The present process involving palladium catalyzed coupling of a 3-sulfonyloxycephem with an organic stannane is particularly preferred for the preparation of cefprozil. The starting stannane, Z-1-propenyl trialkylstannane, for the synthesis of cefprozil may be obtained from cis-1-bromopropene, and an efficient process for preparing isomerically pur (>99%) cis-1-bromopropene has been developed and is provided herein below.

Preparation of cis-1-bromopropene. A 500 mL flask equipped with an overhead stirrer, thermometer and addition funnel was charged with crotonic acid (51.68 g, 0.6 mol, Aldrich) and 320 mL of heptane. The resulting mixture was brought to a reaction temperature of 30° C. (warm water bath) under a blanket of dry nitrogen. Next, 34.4 mL (0.63 mol, 1.05 equiv) of bromine (Fisher) was added dropwise over ca. 45 min while maintaining a reaction temperature of 30° C. (cold water bath). Within 4 to 5 min. after complete addition, crystallization of the product, erythro-2,3-dibromobutyric acid, commenced. A cold water bath was applied to maintain a reaction temperature of ca. 34° C. The mixture was brought to ambient temperature, stirred an additional 16 hr. and cooled in an ice water bath for 30 min. The colorless crystals were collected by suction filtration, washed with heptane (2×75 mL) and dried in vacuo at ambient temperature to constant weight to afford 130 g (88%) of erythro-2,3-dibromobutyric acid, mp 87°–89° C.

A 2 L flask equipped with an overhead stirrer, thermometer and reflux condenser with a mineral oil bubbler attached to the top of the condenser was charged with 517.5 mL (3.71 mol, 4.13 equiv) of 99% triethylamine (Aldrich). With vigorous stirring, a total of 221.33 g (0.90 mol) of erythro-2,3-dibromobutyric acid was added in ten portions at five min. intervals. During this addition period, gas evolution (bubbler) and an exotherm to 40° C. were noted. The reaction mixture was stirred at ambient temperature for 3.4 hr followed by heating at 40° C. for an additional 3.5 hr (gas evolution complete). The mixture was cooled to ambient temperature and 321 mL of water was added. Solids were rinsed in and allowed to dissolve. Next, 230 mL of conc. HCl solution (Fisher) was added while maintaining a reaction temperature of 0° C. Separation of the lower phase in a separatory funnel gave 82.15 g (75%) of crude cis-1-bromopropene. The aqueous phase was saved for recovery of triethylamine.

The crude product was washed with an equivalent volume of saturated $NaHCO_3$ solution and distilled at atmospheric pressure to afford isomerically pure cis-1-bromopropene as a colorless liquid: bp 59°–60° C.

The acidic aqueous phase was cooled to 0°–5° C. and 750 mL of 25% aqueous NaOH solution was added dropwise with good stirring. Separation of the upper phase in a separatory funnel affordedna quantitative recovery of the triethylamine.

The products of formula III wherein Q is the carboxyacyl group of a known 7-acylaminocephalosporin antibiotic are themselves antibiotic compounds useful for the treatment of infections caused by bacteria, and other sensitive microorganisms. The antibiotic products are not, however, considered part of this invention which is directed to process and intermediates.

Those products, of formula III wherein Q is H or a protecting group are intermediates for producing the aforesaid antibiotic compounds of formula III through the agency of acylation, or deprotection and acylation as is known to those skilled in the art.

The following examples illustrate the preparation of various 3-$R^1$ substituted ceph-3-ems of formula III by the process of the present invention from the corresponding 3-sulfonyloxyceph-3-ems referred to above. These examples are not to be construed as limiting the scope of the invention in any manner.

Procedure 1

Diphenylmethyl 7-Phenoxyacetamido-3-[(4-nitrophenylsulfonyloxy]-3-cephem-4-carboxylate.

A solution of 0.516 g (0.001 mole) of diphenylmethyl 7-phenoxyacetamido-3-hydroxy-3-cephem-4-carboxylate in 5 mL of dry tetrahydrofuran was cooled to 0° C. under a nitrogen atmosphere. Then 0.040 g (0.001 mole) of sodium hydride (60% in mineral oil) was added resulting in hydrogen evolution. The reaction mixture was stirred at 0° C. for 5 minutes and 0.221 g (0.001 mole) of 4-nitrobenzenesulfonyl chloride was added. The reaction mix was stirred at 0° C. for 1 hour and at room temperature for 19 hours. The solvent was removed at reduced pressure and replaced with 30 mL of ethyl acetate. This solution was washed (3×) with water the the organic phase concentrated in vacuo to a foam residue. The residue was purified by silica gel chromatography to yield 0.5 g (71%) of the title compound.

Analytical Data $^1$H-NMR (CDCl$_3$, 360 MHz): δ8.15 (d, 2H); 7.7 (d, 2H); 7.4–6.9 (m, 16H); 6.72 (S, 1H), 5.95 (dd, 1H), 5.3 (d, 1H); 4.55 (S, 2H); 3.9 (d, 1H); 3.58 (d, 1H).

Procedure 2

Diphenylmethyl 7-Phenoxyacetamido-3(Z-1-propenyl)-3-cephem-4-carboxylate.

To a mixture of 1.75 g (0.0025 mole) of the product of Procedure 1, 1.03 g (0.003125 mole) of Z-1-propenyl-tri-n-butylstannane and 0.06 g (0.00025 mole) of 4-nitrobenzenesulfonyl chloride in 17.5 mL of 1-methyl-2-pyrrolidinone under a nitrogen atmosphere, at room temperature was added 0.06 g (0.00025 mole) of palladium (II) acetate. The reaction mix was stirred at room temperature for 19 hours. The reaction solution was diluted with 125 mL of ethyl acetate and the organic phase washed (3×) with water. The ethyl acetate solution was carbon treated and the carbon removed by filtration through a celite pad. The solvent was removed at reduced pressure and the residue was filtered through a silica gel pad with 50% ethyl acetate/n-hexane. The crude product was crystallized from 2-propanol yielding 1.031 g (76%) of the title compound.

Analytical Data $^1$H-NMR (CDCl$_3$3, 360 MHz): δ 7.4–6.8 (m, 17H), 6.1 (br d, 1H); 5.85 (dd, 1H), 5.55 (m, 1H); 5.05 (d, 1H), 4.58 (S, 2H); 3.43 (d, 1H); 3.25 (d, 1H).

Procedure 3

Diphenylmethyl 7-Phenoxyacetamido-3-[(fluorosulfonyl)oxy]-3-cephem-4-carboxylate A solution of diphenylmethyl 7-phenoxyacetamido-3-hydroxy-3-cephem-4-carboxylate (2.0 g, 3.8 mmole) in dichloromethane (20 mL) was cooled to −78° C. under an inert atmosphere. N,N-diisopropylethyl amine (0.74 mL, 4.2 mmol, 1.1 eq.) was added dropwise over a 2 minute period. The resulting pale yellow solution was allowed to stir for 5 minutes then treated with fluorosulfonic anhydride (0.77 g, 4.2 mmole, 1.1 eq.). The reaction was allowed to stir for 30 minutes then was quenched by addition of water (10 mL). After warming to ambient temperature, the organic phase was dried over magnesium sulfate and the resulting solution was filtered through a short pad of silica gel. The silica pad was rinsed with ethyl acetate (10 mL) and the combined organic fractions were concentrated to furnish 2.3 g of a pale yellow foam. The crude product was crystallized from diethyl ether to afford 2.2 g (96%) of the title compound as white needles, m.p. 131°–132° C. dec.

Analytical Data $^1$H NMR (360 MHz, CDCl$_3$) δ 7.42–7.24 (complex M, 13H); 7.03 (apparent t, 2H); 6.90 (d, 2H, J=7.9 Hz); 5.97 (dd, 1H, J=5.0, 9.2 Hz); 5.08 (d, 1H, J=5.0 Hz); 4.55 (S, 2H); 3.83 (A of AB, 1H, J=18.5 Hz); 3.51 (B of AB, 1H, J=18.5 H, J=18.5 Hz).
$^{13}$C NMR (90.5 MHz, CDCl$_3$): δ168.63; 164.26; 157.62; 156.73; 139.94; 138.46; 138.28; 129.89; 128.57; 128.51; 128.44; 128.34; 127.76; 127.25; 122.55; 114.71; 80.60; 66.98; 58.23; 57.33; 25.58.

Anal. Calcd. for C$_{28}$H$_{23}$FN$_2$O$_8$S$_2$: C, 56.17; H, 3.87; N, 4.68. Found: C, 55.88; H, 3.94; N, 4.56.

Procedure 4

Diphenylmethyl 7-Phenoxyacetamido-3-vinyl-3-cephem-4-carboxylate.

A solution of palladium (II) acetate (3.6 mg, 0.016 mmol, 0.1 eq.) in 1-methyl-2-pyrrolidinone (2 mL) was treated with vinyl tri-n-butylstannane (58.4 mL, 0.2 mmol, 1.2 eq.) under an inert atmosphere and allowed to stir for 3 minutes. The resulting dark suspension was then treated with diphenylmethyl 7-phenoxyacetamido-3-[(fluorosulfonyl)oxy] -3-cephem-4-carboxylate (100.0 mg, 0.16 mmol, 1.0 eq.) in one portion and the reaction mixture was allowed to stir for 10 minutes. The reaction mixture was diluted with ethyl acetate and washed with 3×20 mL of water. The organic fraction was dried over magnesium sulfate then concentrated. The crude brown residue was purified by flash filtration through a pad of silica gel (W. R. Grace, 951W) first with dichloromethane (50 mL) to remove the residual stannane and then with 10% ethyl acetate in dichloromethane (75 mL), which upon concentration furnished 74.8 mg (85%) of the title compound as a white solid.

Analytical Data $^1$H NMR (360 MHz, CDCl$_3$): δ7.42–7.23 (complex m, 12H); 7.04–6.92 (complex m, 2H); 6.91 (d, 1H, J=7.82 Hz); 5.90 (dd, 1H, J=4.9, 9.2 Hz); 5.42 (d, 1H, J=17.6 Hz); 5.26 (d, 1H, J=11.2 Hz); 5.02 (d, 1H, J=4.9 Hz); 4.55 (s, 2H); 3.62 (A of AB, 1H, J=17.7 Hz); 3.46 (B of AB, 1H, J=17.7 Hz).
$^{13}$C NMR (90.5 MHz, CDCl$_3$): δ168.66; 164.19; 161.00; 156.82; 139.28; 139.01; 131.79; 129.77; 128.51; 128.39; 128.16; 128.04; 127.72; 127.54; 127.01; 126.48; 122.32; 118.07; 114.69; 79.37; 67.01; 58.47; 57.27; 24.09.

Procedure 5

Diphenylmethyl 7-Phenoxyacetamido-3-(Z-1-propenyl)-3-cephem-4-carboxylate.

A solution of palladium (II) acetate (3.6 mg, 0.016 mmole, 0.1 eq.) in dichloromethane (2 mL) was treated with Z-1-propenyl tri-n-butylstannane (66.2 mg, 0.2 mmole, 1.2 eq.) under an inert atmosphere and allowed to stir for 3 minutes. The resulting dark suspension was then treated with diphenylmethyl 7-phenoxyacetamido-3-[(fluorosulfonyl)oxy]-3-cephem-4-carboxylate (100.0 mg, 0.16 mmole, 1.0 eq.) in one portion and the reaction mixture was allowed to stir for 10 minutes. The reaction mixture was diluted with additional dichloromethane and washed with water (1×10 mL). The organic fraction was dried over magnesium sulfate and purified by flash filtration through a pad of silica gel (W. R. Grace, 951W) first with dichloromethane (50 mL) to remove the residual stannane and then with 10% ethyl acetate in dichloromethane (50 mL) which upon concentration furnished 80.4 mg (89%) of the title compound as a pale yellow solid. The product was then recrystallized from isopropyl alcohol to afford 62.3 mg (69%) of a white solid, mp. 103°–104° C.

Analytical Data $^1$H NMR (360 MHz, CDCl$_3$): δ7.41–6.90 (complex M, 17H); 6.10 (d, 1H, J=11.7 Hz); 5.90 (dd, 1H, J=4.5, 9.8 Hz);5.56 (m, 1H; 5.07 (d, 1H, J=4.5 Hz); 4.58 (S, 2H);

3.47 (A of AB, 1 H, J=17.5 Hz); 3.28 (B of AB, 1H, J=17.5 Hz); 1.41 (dd, 3H, J=1.7, 7.1 Hz).

$^{13}$C NMR (90.5 MHz, CDCl$_3$): δ168.63; 164.28; 161.28; 156.83, 139.42; 139.10; 130.33; 129.80; 129.74; 128.45; 128.28; 128.08; 127.79; 127.81; 127.18; 125.88; 122.37; 114.74 ;78.99; 67.06; 58.45 ;57.55; 28.50.

Procedure 6

Diphenylmethyl 7-Phenoxyacetamido-3-[(4-bromophenylsulfonyl)oxy]-3-cephem-4-carboxylate.

The title compound was prepared via a modification of the synthesis described in U.S. Pat. No. 3,985,737. A solution of 0.51 g (0.001 mole) of diphenylmethyl 7-phenoxyacetamido-3-hydroxy-3-cephem-4-carboxylate in 5 mL of acetonitrile was cooled to 0° C. under a nitrogen atmosphere. Then 0.030 g (0.001 mole) of sodium hydride (80% in mineral oil) was added resulting in hydrogen evolution. The reaction mixture was stirred at 0° C. for 5 minutes, and 0.229 g (0.009 mole) of 4-bromobenzenesulfonyl chloride was added. The cooling bath was removed, and the reaction mix stirred at room temperature for 19 hours. The reaction mixture was filtered and the filtrate carbon treated. The carbon was removed followed by the solvent to leave a foam residue. The residue was crystallized from 1-propanol to yield 0.398 g (54%) of the title compound.

Analytical Data $^1$H NMR (CDCl$_3$, 360 MHz): δ7.5 (d, 2H); 7.4 (d, 2HO), 7.4–6.9 (m, 16H), 6.79 (s, 1H); 5.9 (dd, 1H), 5.1 (d, 1H), 4.55, (s, 2H); 3.85 (d, 1H), 3.5 (d, 1H).

Procedure 7

Diphenylmethyl 7-Phenoxyacetamido-3-(Z-1-propenyl)-3-cephem-4-carboxylate.

To a mixture of 0.184 g (0.00025 mole) of the product of Procedure 6, 0.103 g (0.0003215 mole) of Z-1-propenyl-tri-n-butylstannane and 0.0064 g (0.000025 mole) of 4-bromobenzenesulfonyl chloride in 2.5 mL of 1-methyl-2-pyrrolidinone, under a nitrogen atmosphere, at room temperature was added 0.006 g (0.000025 mole) of palladium (II) acetate. The reaction mix was stirred at room temperature for 20 hours. High pressure liquid chromatography (HPLC) analysis of the reaction mixture showed a peak for the title compound with retention time identical to an authentic sample of the title compound. The HPLC area percent for this peak was 21.2%

Procedure 8

Diphenylmethyl 7-phenoxyacetamido-3-(Z-1-propenyl)-3-cephem-4-carboxylate via Tris(dibenzylideneacetone)dipalladium(0).

A solution of tris(dibenzylideneacetone)dipalladium (14.6 mg, 0.016 mmole, 0.1 eq.) in either dichloromethane (2 mL) or 1-methyl-2-pyrrolidinone (2 mL) was treated with Z-1-propenyl tri-n-butylstannane (66.2 mg, 0.2 mmole, 1.2 eq.) under an inert atmosphere. The resulting solution was then treated with diphenylmethyl 7-phenoxyacetamido-3-[(fluorosulfonyl)oxy]-3-cephem-4-carboxylate (100.0 mg, 0.16 mmole, 1.0 eq.) in one portion, and the reaction was monitored by HPLC. The reaction run in dichloromethane was complete within 3 hours, while the reaction run in 1-methyl-2-pyrrolidinone was complete within 8 hours. Yields of the desired product were >98% as determined by HPLC, and NMR analysis at 360 MHz of the products from both reaction solvents was consistent with the named compound.

Procedure 9

Diphenylmethyl 7-Phenoxyacetamido-3-(Z-1-propenyl)-3-cephem-4-carboxylate via Tris(dibenzylideneacetone)dipalladium(0)

To a mixture of 0.175 g (0.00025 mole) of the product of Procedure 1, 0.099 g (0.0003 mole) of Z-1-propenyl-tri-n-butylstannane in 1.0 mL of 1-methyl-2-pyrrolidinone, under a nitrogen atmosphere, at room temperature was added 0.014 g (0.000025 mole) of tris(dibenzylideneacetone) dipalladium(0). The reaction mix was stirred at room temperature for 17 hours. The reaction mixture was diluted with ethyl acetate and the organic phase washed (2×) with water. The ethyl acetate solution was carbon treated and the carbon removed by filtration through a celite pad. The solvent was removed in vacuo to a foam residue. The residue was purified by silica gel chromatography to yield 0.060 g (44%) of the title compound. The nuclear magnetic resonance spectrum was consistent for the named compound.

Procedure 10 t-Butyl 7-(benzyloxycarbonylamino)-3-fluorosulfonyloxy-1carba(1-dethia)-3-cephem-4-carboxylate.

A 1.36M solution of fluorosulfonyl anhydride in methylene chloride (665 μL, 0.906 mmol) was added dropwise to a stirred, cooled (CO$_2$/acetone bath) solution of t-butyl 7-(benzyloxycarbonylamino)-3-hydroxy-1-carba(11-dethia)-3-cephem-4-carboxylate (352 mg, 0.906 mmol) and diisopropylethylamine (158 μL, 0.906 mmol) in methylene chloride (5 mL). The solution was stirred at −78° C. for 0.25 hr. when the cooling bath was removed and stirring continued at ambient temperatures for 0.25 hr. The solution was washed three times with H$_2$O and then was dried over sodium sulfate. Removal of the solvent left a viscous gum which was chromatographed on SiO$_2$ (20 g) with methylene chloride-ethyl acetate (95:5) to provide the title compound (130 mg, 30% yield) as a viscous gum, which was crystallized from ethyl acetate-hexanes to afford colorless crystals (56 mg), mp 118° C. (decomp.).

Analytical Data $^1$HN MR (CDCl$_3$, 300 MHz) δ7.35 (5H, s) , 5.37 (1H, m), 5.22 (1H, m), 5.11 (2H, s), 3.87 (1H,m), 2.65 (2H, m), 2.13 (1H, m), 1.68 (1H, m), 1.53 (9H, s).

Mass Spectrum: (positive ion FAB, NOBA) m/z 471 (M+1).

What is claimed is:

1. A compound having the formula

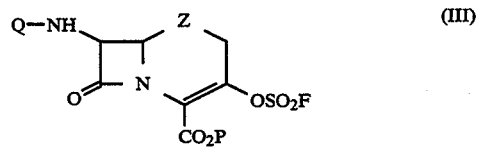

(III)

wherein
Z is methylene;
Q is hydrogen, an amine protecting group conventionally used in cephalosporin synthesis, or R—C(O)— wherein R is selected form the group consisting of:

wherein G is selected from the group consisting of phenyl, thienyl, thiazolyl, thiadiazolyl, imidazolyl, pyridyl, tetrazolyl, 1,4-cyclohexadienyl, and furyl; each is optionally substituted with from 1 to 3 of the same or different groups selected from halogen, hydroxy, amino, alkoxy, alkylamino, dialkylamino, alkanoyloxy, carboxy, nitro, cyano, and alkoxycarbonyl; G' is selected from the group consisting of hydrogen, hydroxy, amino, monoalkylamino, dialkylamino, alkanoylamino, alkanoyloxy, carboxy, and sulfo;

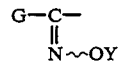

wherein G has the same meaning given above, and Y is hydrogen, $C_{1-6}$alkyl, or $C_{1-6}$alkanoyl;

(c) G—B—CH$_2$— wherein G has the same meaning given above, and B is oxygen or sulfur; and

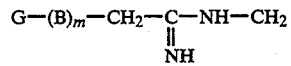

where G, and B have the meanings given above, and m is 0 or 1; and

P is hydrogen, a carboxy protecting group conventionally used in cephalosporin synthesis, a cation, or a physiologically hydrolyzable ester.

2. t-Butyl 7-[(benzyloxycarbonyl)amino]-3-[(fluorosulfonyl)oxy]-1-carba(1-dethia)-3-cephem-4-carboxylate.

* * * * *